United States Patent [19]

Guillemet

[11] Patent Number: 5,527,535
[45] Date of Patent: Jun. 18, 1996

[54] PROCESS FOR THE MANUFACTURE OF A DRESSING WITH THINNED EDGES

[75] Inventor: Alain Guillemet, Fontaine-lès-Dijon, France

[73] Assignee: Laboratoires D'Hygiene et de Dietetique, Paris, France

[21] Appl. No.: 256,838

[22] PCT Filed: Jan. 11, 1993

[86] PCT No.: PCT/FR93/00021

§ 371 Date: Jul. 28, 1994

§ 102(e) Date: Jul. 28, 1994

[87] PCT Pub. No.: WO93/14726

PCT Pub. Date: Aug. 5, 1993

[30] Foreign Application Priority Data

Jan. 29, 1992 [FR] France ................. 92 00936

[51] Int. Cl.⁶ ................. A61F 13/00; A61K 9/70
[52] U.S. Cl. ................. 424/443; 424/445; 424/446; 424/448
[58] Field of Search ................. 424/443, 402, 424/448, 446, 445

[56] References Cited

U.S. PATENT DOCUMENTS

| | | | |
|---|---|---|---|
| 4,759,354 | 7/1988 | Quarfoot | 424/445 |
| 4,909,244 | 3/1990 | Quarfoot et al. | 602/48 |
| 5,066,494 | 11/1991 | Becher | 424/448 |
| 5,238,685 | 8/1993 | Wren | 424/445 |
| 5,350,581 | 9/1994 | Kochinke | 424/443 |

FOREIGN PATENT DOCUMENTS

| | | |
|---|---|---|
| 0264299 | 4/1988 | European Pat. Off. . |
| 0358412 | 3/1990 | European Pat. Off. . |

*Primary Examiner*—Thurman K. Page
*Assistant Examiner*—William E. Benston, Jr.
*Attorney, Agent, or Firm*—Evenson, McKeown, Edwards & Lenahan

[57] ABSTRACT

A dressing with thinned edges comprising a support and an adhesive system of reducing thickness in the direction of the periphery and a process of making the dressing. The process includes the formation of an adhesive system consisting of at least two adhesive layers which are:

(i) superimposed to form a set of reducing surface areas from the base, joined to the support, to the top, and (ii) arranged in such a way that two adjacent adhesive layers are joined together and have different surface areas, the edges of one of the two adjacent adhesive layers being offset relative to the edges of the other adhesive layer, the adhesive layer forming the base of the adhesive system, which is joined to the support, having a surface area which is (a) identical to that of the support and (b) greater than the surface area of every other layer of the adhesive system.

15 Claims, 1 Drawing Sheet

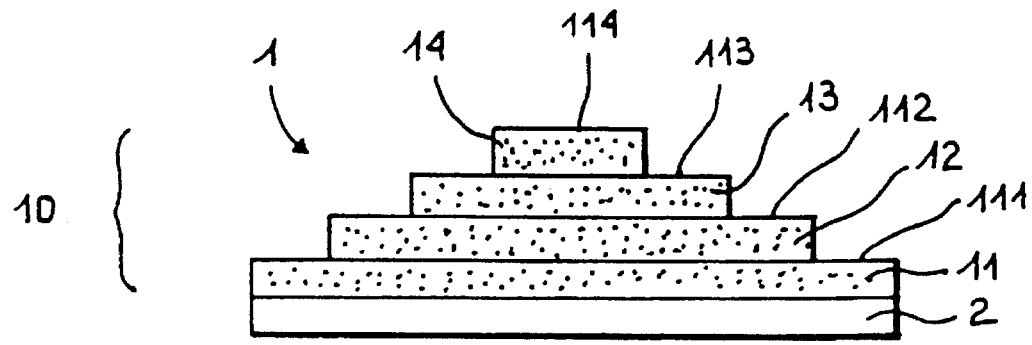
FIG_1
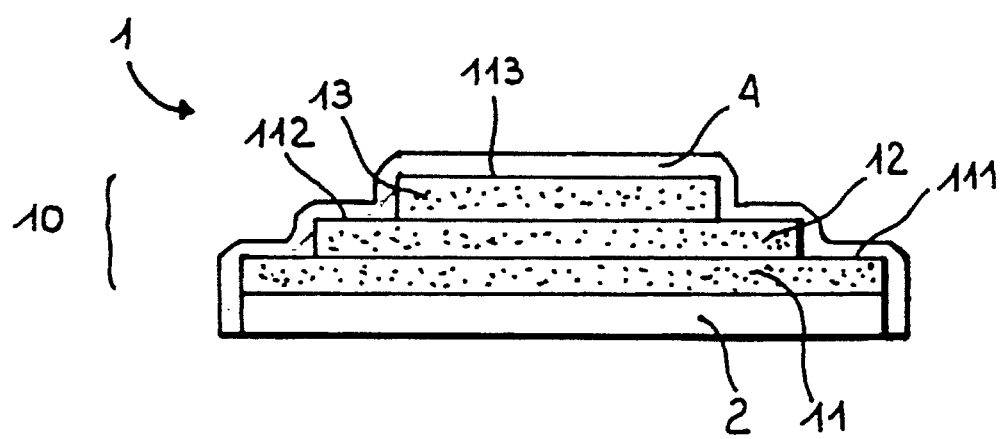
FIG_2
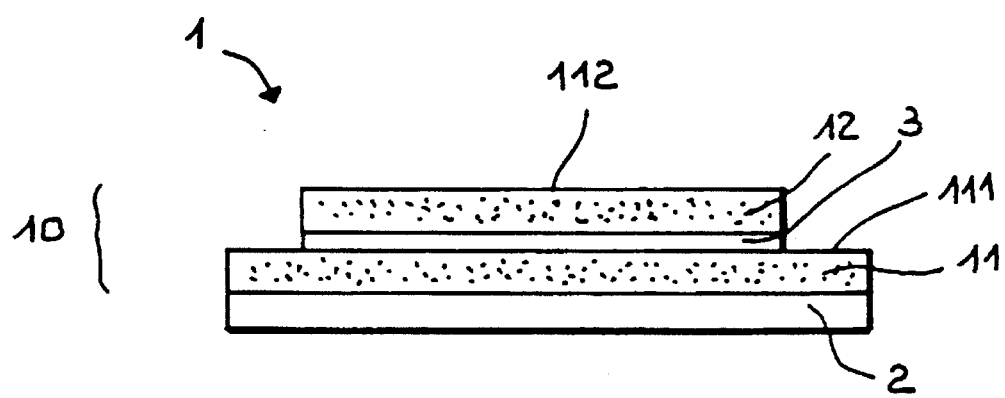
FIG_3

PROCESS FOR THE MANUFACTURE OF A DRESSING WITH THINNED EDGES

FIELD OF THE INVENTION

The present invention relates to a process for the manufacture of a dressing with thinned edges. It further relates, by way of a novel industrial product, to the dressing obtained by this process.

PRIOR ART

EP-A-0 264 299 has disclosed a dressing of the type comprising a support and an adhesive material consisting of a single adhesive layer, in which the edges are chamfered so that the external thickness of the dressing, measured at the periphery, does not exceed ¼ of the thickness of the dressing in its non-thinned part. The essential advantage of such a dressing is that of avoiding creep of the constituent mass of the dressing.

To manufacture this dressing, EP-A-0 264 299 proposes chamfering the edges of the dressing under drastic conditions by applying a "pressure of 10 to 40 metric tonnes" and a temperature of 90 to 110° C. for 1 to 3 seconds, to the periphery of a pad consisting of the support covered with the adhesive layer.

EP-A-0 358 412 has disclosed a dressing with thinned edges which has a stepped profile from the base to the top and comprises three distinct assemblies. According to the description (see column 2 line 50 to column 3 line 45), the FIGS. (1 and 2) and the reference numbers (reproduced below) of EP-A-0 358 412, these assemblies are as follows:

(a) at the base, a first assembly consisting of a nonwoven support (reference 10) covered on its top face with an adhesive layer (reference 11);

(b) on top of the first assembly but with smaller dimensions (length and width) than the latter, a second assembly consisting of a film (reference 12) which on the one hand is joined by its lower face to the first assembly via the adhesive layer (reference 11) of said first assembly, and which on the other hand is covered with an adhesive layer (reference 16) on its top face; and (c) at the top and on top of the second assembly but with smaller dimensions (length and width) than the latter, a third assembly consisting of a layer of superabsorbent material (reference 18) lined with a nonwoven (reference 20), said third assembly being joined to the second assembly via the adhesive layer (reference 16) of said second assembly.

At the time of use, the dressing according to EP-A-0 264 299 is attached to the skin via the exposed zones of the adhesive layers of the first and second assemblies.

The technical solutions known in the prior art are found to be impractical. In fact, the solution proposed by EP-A-0 264 299 for avoiding creep involves a drastic treatment as regards the compression required for chamfering, and the solution proposed by EP-A-0 358 412, which is concerned neither with limiting nor with eliminating creep, has the disadvantage on the one hand of increasing the thickness of the dressing at its center, and on the other hand of not being adhesive at its top (i.e. on the upper face of the third assembly).

OBJECT OF THE INVENTION

According to the invention, a novel technical solution is now proposed for avoiding creep of the constituents of the dressing and for mitigating the disadvantages of the prior art.

This novel solution uses at least two adhesive layers superimposed to form a reducing construction from the base to the top, called a stepped construction, the upper layer of this construction, i.e. the one situated at the top, being an adhesive layer.

SUBJECT OF THE INVENTION

According to the invention, a process is therefore recommended for the preparation of a dressing with thinned edges comprising, joined to one another, a support and a film-type adhesive system of reducing thickness in the direction of the periphery, said process comprising the formation of an adhesive system consisting of at least two adhesive layers which are (i) superimposed to form a set of reducing surface areas from the base, joined to the support, to the top, and (ii) arranged in such a way that two adjacent adhesive layers are joined together and have different surface areas, the edges of one of the two said adjacent adhesive layers being offset relative to the corresponding edges of the other adhesive layer, the adhesive layer forming the base of said adhesive system, which is joined to the support, having a surface area which is (a) identical to that of said support and (b) greater than the surface area of every other layer of said adhesive system.

The invention further relates to a dressing with thinned edges wherein said adhesive system contained therein consists of at least two adhesive layers which are (i) superimposed to form a set of reducing surface areas from the base, joined to the support, to the top, and (ii) arranged in such a way that two adjacent adhesive layers are joined together and have different surface areas, the edges of one of the two said adjacent adhesive layers being offset relative to the corresponding edges of the other adhesive layer, the adhesive layer forming the base of said adhesive system, which is joined to the support, having a surface area which is (a) identical to that of said support and (b) greater than the surface area of every other layer of said adhesive system.

BRIEF DESCRIPTION OF THE DRAWINGS

In the attached drawings:

FIG. 1 is a schematic representation, in section, of a dressing with thinned edges according to the invention containing four adhesive layers;

FIG. 2 is a schematic representation, in section, of a dressing with thinned edges according to the invention containing three adhesive layers, the exposed zones of which are covered with a peel-off protective layer; and FIG. 3 is a schematic representation, in section, of a dressing with thinned edges according to the invention containing two adhesive layers of different types separated from one another by a film.

DETAILED DESCRIPTION OF THE INVENTION

With reference to FIGS. 1, 2 and 3, the dressing 1 according to the invention is of the type comprising a support 2 and an adhesive system 10. The adhesive system 10 consists of at least two adhesive layers (i.e. in particular:

two adhesive layers 11, 12 for the dressing of FIG. 3; three adhesive layers 11, 12, 13 for the dressing of FIG. 2; and four adhesive layers 11, 12, 13, 14 for the dressing of FIG. 1). For practical purposes, the total number of adhesive layers used will be two, three or four. In fact, the advantages which might be gained by a "construction" containing more than four adhesive layers would not justify the resulting increase in production costs. The dressing according to the invention will preferably comprise two or three adhesive layers.

The thickness of the adhesive system 10 decreases in the direction of the periphery when measured in a vertical plane passing through the vertical axis of the dressing. According to FIG. 1, this thickness corresponds to the sum of the thicknesses of the four layers 11–14 in the portion closest to the axis of the dressing, then to the sum of the thicknesses of the lower layers 11–13 and 11–12 on moving away from the axis, and finally to the thickness of the first layer 11 in the portion furthest away from said axis.

For the sake of convenience, the lower layer 11, which is also called the first layer, is in this case the one covering the support 2 [after the dressing has been placed on the skin, it will be the one furthest away (at the center of the dressing) from the skin], and the upper layer 12, 13 or 14, which is also called the last layer, is in this case the one situated at the top of the construction of stepped profile of the adhesive system 10 [after the dressing has been placed on the skin, it will be the one furthest away from the support 2 and closest to the skin].

The adhesive layers are superimposed to form a set of reducing surface areas from the base to the top and arranged so that two adjacent adhesive layers 11/12, 12/13 or 13/14 are joined together, the edges of the upper adhesive layer 12, 13 or, respectively, 14 being offset relative to those of the adjacent lower layer 11, 12 or, respectively, 13. In other words, when considering two adjacent adhesive layers, the surface area of the upper layer is smaller than that of the adjacent lower layer. The construction which results from the superimposition of said adhesive layers gives the adhesive system 10, and hence the dressing 1, a reducing stepped profile from the base (which has the largest surface area) to the top (which has the smallest surface area).

The first adhesive layer 11 covers the support 2 and has a surface area identical to that of said support. The surface areas of the first layer 11 and the support 2 are made equal by cutting the composite consisting of said support 2 covered with said first adhesive layer 11.

The support 2 can have any constitution known to those skilled in the art in the field of dressings, especially (i) a polyurethane film weighing between 15 g/m² and 80 g/m², (ii) a synthetic nonwoven weighing between 5 g/m² and 50 g/m², which is made for example of polyamide, polyester, polyethylene or polypropylene fibers, or else (iii) a complex (or composite layer) formed of a nonwoven covered with a polyurethane film.

The adhesive layers 11, 12, 13 and 14 each consist of a pressure-sensitive adhesive mass (i.e. self-adhesive mass) known in the field of dressings, which is preferably hypoallergenic. The following are particularly suitable: acrylic adhesive masses such as the polymers and copolymers obtained from the monomers $C_1$–$C_4$-alkyl acrylate and $C_1$ –$C_4$-alkyl methacrylate, adhesive masses such as the copolymers obtained from the monomers ethylene, propylene and vinyl acetate, and mixtures of such masses. The following are also suitable: adhesive masses consisting on the one hand of mixtures of three-block copolymers [of the type comprising a single chain unit of three blocks, such as polystyrene/polyolefin/polystyrene, where the central block (i.e. the polyolefin fragment) is advantageously totally saturated], plasticizers and, if necessary, at least one tackifier (especially an acrylate material because said three-block copolymers are non-adhesive or only slightly adhesive), such mixtures being described especially in French patent application A-2 678 513 (published on 8th Jan. 1993) and the corresponding foreign patent applications, especially U.S. patent application Ser. No. 903 520 (filed on 24th Jun. 1992) and European patent application A-0 521 761 (published on 7th Jan. 1993), and/or on the other hand mixtures of synthetic polymers, for example polyisobutylenes, with hydrocolloids, for example polyvinyl alcohol, pectin, gelatin or sodium carboxymethylcellulose.

On the one hand the adhesive layers 11 and 12, and on the other hand the additional layers 13 and 14 when they are present, can be either of the same type (i.e. they contain the same essential ingredients) or of different types (i.e. they do not contain the same essential ingredients).

When two adjacent adhesive layers are of different types, it is recommended to separate them with an interposed film 3 having a surface area identical to that of the upper layer, whose edges are offset relative to the edges of the larger surface area of the lower layer, as shown in FIG. 3. Such a film 3 can be made of polyethylene, polypropylene or polyurethane, like the support 2.

For practical purposes, if they are present, the additional adhesive layers 13 and, where appropriate, 14 will be of the same type as the second adhesive layer 12 and preferably identical to said second layer 12 from the point of view of composition and thickness.

The first adhesive layer 11 and the second adhesive layer 12 will be either of the same type or of different types, a separating film 3 being placed at their interface in the latter case.

Advantageously, each adhesive layer 11, 12, 13 or 14 will have a thickness of between 100 and 800 micrometers. Preferably, the first adhesive layer 11 will have a thickness of 100 to 400 micrometers, the second adhesive layer 12 will have a thickness of 100 to 800 micrometers when no other adhesive layer is superimposed thereon and a thickness of 100 to 400 micrometers when a third layer 13 is superimposed thereon, and, when they are present, the additional layers 13 and, where appropriate, 14 will have a thickness of 100 to 400 micrometers.

By way of a further preference, on the one hand the film 3 will have a thickness of 15 to 20 micrometers when it is made of polyethylene or polypropylene or a thickness of 15 to 25 micrometers when it is made of polyurethane, and on the other hand the support 2 will have a thickness of 10 to 50 micrometers and preferably 15 to 30 micrometers when it is presented in the form of a polyethylene, polypropylene or, preferably, polyurethane film.

The stepped profile enables the dressing 1 with thinned edges according to the invention to be attached to the skin via the exposed zones 111, 112, 113 and 114 of the adhesive layers 11, 12, 13 and 14 according to FIG. 1 (or the zones 111, 112 and 113 according to FIG. 2, or else the zones 111 and 112 according to FIG. 3).

Also advantageously, said exposed zones will be covered with a non-stick protective layer for storage purposes before the dressing with thinned edges according to the invention is used. In other words, the process for the preparation of the dressing 1 comprises covering the exposed zones with a non-stick protective layer 4, this protective layer being temporary and removable by lifting or peeling at the time when said dressing is placed on the skin.

In a first embodiment of a dressing with thinned edges, it is recommended to place a first thin adhesive layer 11, consisting of a pressure-sensitive and hypoallergenic acrylic mass (copolymer of $C_1$–$C_4$-alkyl acrylate or $C_1$–$C_4$-alkyl methacrylate) on a support 2 by coating or transfer, and then to superimpose, by transfer, a second adhesive layer 12 consisting of a mixture of three-block copolymer (according to French patent application A-2 678 513 cited above), plasticizer and, if necessary, at least one tackifier, or a mixture of synthetic polymers and hydrocolloids, whose surface area is less than the surface area of the first layer in the sense that it is offset relative to the outer edges of said first layer 11 by a distance of between about 0.2 and 1.5 cm in particular.

In a first variant of this first embodiment, a flexible film 3, whose surface area is identical to the surface area of the second adhesive layer 12, is interposed between the first adhesive layer 11 and said second layer 12 so that the zone 111 of the upper face of the adhesive mass of the first layer 11 is left exposed.

In a second variant of said first embodiment, said second adhesive layer 12, which then has a thickness of between 100 and 400 micrometers, is covered with a third adhesive layer 13. This adhesive layer 13 is of the same type and thickness as said second layer 12, but has a smaller surface area than said second layer 12, the edges of the third adhesive layer 13 being offset relative to the outer edges of the second adhesive layer 12 by a distance of between 0.2 and 1.5 cm in particular.

In a second embodiment of a dressing with thinned edges, it is recommended to place a first thin adhesive layer 11, having a thickness of 100 to 400 micrometers, on a support 2 by coating or transfer, and then to superimpose, by transfer, a second adhesive layer 12 of a type identical to that of the first layer 11, having a thickness of between 100 and 800 micrometers and a smaller surface area than the first layer, the two adhesive layers 11 and 12 consisting especially of a mixture of three-block copolymers, plasticizers and, if necessary, at least one tackifier, or a mixture of synthetic polymers, especially of the polyisobutylene type, and hydrocolloid compounds, and the edges of the second adhesive layer 12 being offset relative to the outer edges of said first layer 11 by a distance of between about 0.2 and 1.5 cm in particular.

The dressing 1 according to the invention will advantageously be produced with a simple geometric shape having at least one axis or one plane of symmetry. In particular, it will be:

- inscribed in a truncated pyramid, in which case its base (i.e. the adhesive layer 11 and the support 2) will be polygonal (square or rectangular),
- inscribed in a truncated cone, in which case its base will be curvilinear (especially circular, oval or elliptical), or
- inscribed in a mixed surface of the truncated pyramid/truncated cone type, in which case its base will comprise at least one rectilinear portion and at least one curvilinear portion.

BEST MODE

The best mode of carrying out the process according to the invention for the preparation of a dressing with thinned edges containing two adhesive layers 11 and 12 comprises, from an industrial point of view, three successive steps consisting in:

(1°) placing a first adhesive layer 11 on a support 2 by a solvent-phase coating technique or a so-called "molten method" technique, depending on the type of said first adhesive layer 11, and covering said first adhesive layer 11 with a non-stick temporary support, especially a piece of siliconized paper;

(2°) placing a second adhesive layer 12 on a final nonstick protective layer 4, especially by said so-called "molten method" technique, and, if necessary, covering with a flexible film 3 that face of said second adhesive layer 12 which is not covered with said non-stick protective layer 4; and (3°) forming the dressing by cutting the composite obtained in step (2°) to the requisite dimensions, cutting said non-stick protective layer 4, applying said composite obtained in this way to the composite obtained in step (1°) after removal of said non-stick temporary support covering said first adhesive layer 11, and then cutting to the requisite dimensions the non-stick protective layer 4, the first adhesive layer 11 and the support 2 of the resulting assembly comprising said non-stick protective layer 4, said second adhesive layer 12, said first adhesive layer 11 and said support 2.

To prepare a dressing with thinned edges containing more than two adhesive layers, the procedure is as indicated above (in the best mode relating to a dressing with thinned edges having only the adhesive layers 11 and 12), on the one hand with the following modification to step (1°) before application of said non-stick temporary support:

the first adhesive layer 11 is covered with a second adhesive layer 12 which has been cut out beforehand and, if appropriate, provided with said flexible film 3 on its lower face, and said second adhesive layer 12 is covered, if appropriate, with a third layer 13 which has been cut out beforehand, and on the other hand with a modification to step (2°) such that it involves only the formation of the composite containing the upper adhesive layer 13 or 14, step (3°) then involving the cutting of the composite containing the upper adhesive layer, the application of this composite to that obtained in said step 1, and then the final cutting.

Other advantages and characteristics of the invention will be understood more clearly from the following description of Examples, which in no way imply a limitation but are given by way of illustration.

EXAMPLE 1

According to the best mode described above, a dressing with thinned edges is prepared which comprises the adhesive layers 11 and 12. This dressing contains:

as the support 2, a polyurethane film having a thickness of 30 micrometers;

as the first adhesive layer 11, an acrylic mass based on an ethyl acrylate/methyl methacrylate/2-hydroxyethyl methacrylate copolymer and having a thickness of 250 micrometers;

as the separating film 3, a polyethylene film having a thickness of 15 micrometers;

as the second adhesive layer 12, an adhesive mass consisting of a mixture of (i) a polystyrene/polyethylene-butylene/polystyrene three-block copolymer, (ii) petrolatum, (iii) the synthetic resin WINGTACK 95 marketed by GOODYEAR, and (iv) sodium carboxymethylcellulose (CMC) [where the means (i) and (ii), which are not adhesive, are those described in Example 1 of French patent application A-2 678 513 cited above, the means (iii) provides said mass with its adhesive property by virtue of its tackifying power, and the means (iv) provides said mass with its absorbent property]and having a thickness of 450 micrometers; and as a non-stick protective layer 4, a siliconized film.

EXAMPLE 2

According to the best mode described above, a dressing with thinned edges is prepared which comprises three adhesive layers, namely the layers 11, 12 and 13. This dressing contains:

as the support 2, a polyurethane film having a thickness of 50 micrometers;

as the first adhesive layer 11, an acrylic mass based on an ethyl acrylate/methyl methacrylate copolymer and having a thickness of 200 micrometers;

as the separating film 3, a polyurethane film having a thickness of 20 micrometers;

as the second adhesive layer 12, an adhesive mass consisting of the three-block copolymer/petrolatum/synthetic resin/CMC mixture described in Example 1 above and having a thickness of 250 micrometers;

as the third adhesive layer 13, an adhesive mass identical in its composition and thickness to that of the second adhesive layer 12 which it covers; and as a non-stick protective layer 4, a siliconized film.

EXAMPLE 3

In the manner indicated above for Example 2, a dressing with thinned edges is prepared which comprises three adhesive layers 11, 12 and 13. This dressing is identical to that of Example 2 except that (i) the first adhesive layer 11 is an adhesive mass consisting of the three-block copolymer/petrolatum/synthetic resin/CMC mixture described in Example 1 above and having a thickness of 400 micrometers, (ii) the adhesive layers 12 and 13, identical to the layers 12 and 13 of Example 2, each have a thickness of 300 micrometers, and (iii) the flexible film 3 between the adhesive layers 11 and 12 has been omitted.

EXAMPLE 4

In the manner indicated above for Example 2, a dressing with thinned edges is prepared which comprises only two adhesive layers, 11 and 12. The two adhesive layers, which have the same composition, consist of the three-block copolymer/petrolatum/synthetic resin/CMC mixture, the first layer 11 having a thickness of 400 micrometers, the second layer 12 having a thickness of 600 micrometers and the two layers 11 and 12 not being separated by a flexible film.

What is claimed is:

1. A process for the preparation of a dressing which is thinner at the edges than at a central portion comprising a support and an adhesive system of reducing thickness in the direction of the periphery, said process comprising the formation of an adhesive system consisting of at least two adhesive layers which are (i) superimposed to form a set of reducing surface areas from the base, joined to the support, to the top, and (ii) arranged in such a way that two adjacent adhesive layers are joined together and have different surface areas, the edges of one of the two said adjacent adhesive layers being offset relative to the edges of the other adhesive layer, the adhesive layer forming the base of said adhesive system, which is joined to the support, having a surface area which is (a) identical to that of said support and (b) greater than the surface area of every other layer of said adhesive system.

2. A process according to claim 1 in which the formation of said adhesive system involves a first adhesive layer forming the base of said adhesive system, and a second adhesive layer, which contains the same essential ingredients as the first adhesive layer.

3. A process according to claim 1 in which the formation of said adhesive system involves a first adhesive layer forming the base of said adhesive system, and a second adhesive layer which is not the same as the first adhesive layer.

4. A process according to claim 2 in which the additional adhesive layers, which form said adhesive system with the first and second adhesive layers, contain of the same essential ingredients as said second adhesive layer.

5. A process according to claim 3 in which a flexible film is provided in order to separate said first and second adhesive layers when the latter are of different types, said film not covering the zone of the first adhesive layer which is exposed by the superimposition of the second adhesive layer.

6. A process according to claim 1 in which all the adhesive layers of said adhesive system contain the same essential ingredients.

7. A process according to claim 1 wherein the exposed zones of the adhesive layers of said adhesive system (10) are covered with a non-stick protective layer.

8. A process according to claim 1 for the preparation of a dressing which is thinner at the edges than at a central portion containing two adhesive layers and, said process comprising three successive steps consisting in:

(1°) placing a first adhesive layer on a support and covering said first adhesive layer with a non-stick temporary support;

(2°) placing a second adhesive layer on a final non-stick protective layer and, if necessary, covering with a flexible film that face of said second adhesive layer which is not covered with said non-stick protective layer; and (3°) forming the dressing by cutting the composite obtained in step (2°) to the requisite dimensions, cutting said non-stick protective layer, applying said composite obtained in this way to the composite obtained in step (1°) after removal of said non-stick temporary support covering said first adhesive layer, and then cutting to the requisite dimensions the non-stick protective layer, the first adhesive layer and the support of the resulting assembly comprising said non-stick protective layer, said second adhesive layer, said first adhesive layer and said support.

9. A dressing which is thinner at the edges than at a central position comprising a support and an adhesive system of reducing thickness in the direction of the periphery, wherein said adhesive system consists of at least two adhesive layers which are (i) superimposed to form a set of reducing surface areas from the base, joined to the support, to the top, and (ii) arranged in such a way that two adjacent adhesive layers are joined together and have different surface areas, the edges of one of the two said adjacent adhesive layers being offset relative to the edges of the other adhesive layer, the adhesive layer forming the base of said adhesive system, which is joined to the support, having a surface area which is (a) identical to that of said support and (b) greater than the surface area of every other layer of said adhesive system.

10. A process according to claim 3 in which the additional adhesive layers, which form said adhesive system with the first and second adhesive layers, contain the same essential ingredients as said second adhesive layer.

11. A process according to claim 1 in which said adhesive layers comprise a member of the group consisting of:

a) $c_1$–$c_4$-alkyl acrylate and methacrylate polymers and copolymers;

b) ethylene, propylene and vinyl acetate copolymers;

c) mixtures of three-block copolymers of polystyrene/polyolefin/polystyrene and plasticizers;

d) mixtures of synthetic polymers with hydrocolloids; and e) mixtures thereof.

12. A process according to claim 11 in which said mixture of three block copolymers of polystyrene/poleolefin/polystyrene comprises at least one tackifier.

13. A process according to claim 11 in which said synthetic polymer is a polyisobutylene.

14. A process according to claim 11 in which said hydrocolloid is selected from the group consisting of polyvinyl alcohol, pectin, gelatin and sodium carboxymethylcellulose.

15. A process according to claim 1 in which one said adhesive layer is an ethyl/methyl/methacrylate/2-hydroexyethyl methacrylate copolymer and one said adjacent adhesive layer is a mixture of a polystyrene/polyethylene-butylene/polystyrene three-block copolymer, petrolatum, a tackifier and sodium carboxymethylcellulose.

* * * * *